United States Patent [19]

Lee

[11] Patent Number: 5,169,963

[45] Date of Patent: Dec. 8, 1992

[54] DI-(5-HYDROXY-2(5H)2-OXO-4-FURYL)AL-KYLMETHYL-ALPHA,OMEGA ALKANEDIOATES AND N,N-BIS-(5-HYDROXY-2(5H)2-OXO-4-FURYL)ALKYLMETHYL-ALPHA,OMEGA-DIALKANOIC ACID AMIDES AS ANTI-INFLAMMATORY AGENTS

[75] Inventor: Gary C. M. Lee, Laguna Hills, Calif.

[73] Assignee: Allergan, Inc., Irvine, Calif.

[21] Appl. No.: 752,405

[22] Filed: Aug. 30, 1991

[51] Int. Cl.$^5$ .................... C07F 9/09; C07F 9/40; C07D 307/60

[52] U.S. Cl. .................... 549/222; 549/318

[58] Field of Search ............ 549/218, 318, 222

[56] References Cited

U.S. PATENT DOCUMENTS

| | | | |
|---|---|---|---|
| 2,359,096 | 9/1944 | Elderfield | 260/239.5 |
| 2,359,208 | 9/1944 | Elderfield | 260/344 |
| 4,447,445 | 5/1984 | Jacobs | 424/279 |
| 4,786,651 | 11/1988 | Wheeler | 514/460 |
| 4,789,749 | 12/1988 | Jacobs et al. | 549/313 |
| 4,855,320 | 8/1989 | Chatterjee et al. | 514/473 |
| 4,874,782 | 10/1989 | Bonjouklian et al. | 514/473 |
| 4,916,241 | 4/1990 | Hayward et al. | 549/313 |
| 4,935,530 | 6/1990 | Lee | 549/214 |
| 4,977,146 | 12/1990 | Biftu et al. | 549/218 |
| 5,013,850 | 5/1991 | Lee | 549/222 |
| 5,037,811 | 8/1991 | Lee | 514/99 |
| 5,043,457 | 8/1991 | Lee | 549/222 |
| 5,045,564 | 9/1991 | Lee | 514/471 |

FOREIGN PATENT DOCUMENTS

| | | |
|---|---|---|
| 133376 | 2/1985 | European Pat. Off. . |
| 209274 | 1/1987 | European Pat. Off. . |
| 295056 | 6/1987 | European Pat. Off. . |
| 350878 | 1/1990 | European Pat. Off. . |

OTHER PUBLICATIONS

Bonjuklian, et al., Chemical Abstracts, vol. 106, 156260c, p. 670 (1987).
Reynolds, et al., J. Am. Chem. Soc., 110, pp. 5172-5177 (1988).
Tocanne et al., Chemical Abstracts 69 76581k, p. 7146 (1968).
Deems, et al., Biochimica et Biophysica Acta. 917, pp. 258-268 (1987).
Scheuer et al., Journal of American Chemical Society 100:1 p. 307 (Jan. 4, 1978).
Roll et al., Org. Chem. 1988, 53 3276-8.
Negishi et al., J. Org. Chem 45, pp. 5223-5225, (1980).
E. D. de Silva et al., "Tetrahedron Letters", 21:1611-1614 (1980).
Nakagawa et al., "Aldose Reductase Inhibitor from Palaun Sponges", Chem. Abstract 106: 96126b.
Tanaka, et al., The Chemical Society of Japan, Chemistry Letters, pp. 633-636 (1983).
Tanis, et al., Tetrahedron Letters, vol. 25, No. 40, pp. 4451-4454 (1984)-Furans in Synthesis 4. Silyl Furans as Butenolide Equivalents.
Graziano, et al., "Photosensitized Oxidation of Furans", Part 12, Solvent Effects in Thermal Rearrangement of the 2,5-Peroxides of 2,5-Unsubstituted Furans, CA 107: 236559t, 1987.
David Nettleton, et al., Inflammation Research Association, Fifth International Conference Poster Session, Phospholipase A$_2$ Inhibition by Dihydrofuranones, Sep. 23-27, 1990.

Primary Examiner—C. Warren Ivy
Assistant Examiner—Amelia A. Owens
Attorney, Agent, or Firm—Gabor L. Szekeres; Martin A. Voet; Robert J. Baran

[57] ABSTRACT

Compounds of the formula

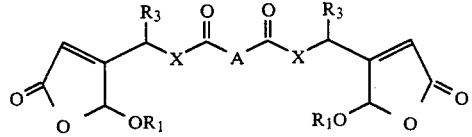

in which R$_1$ independently is H or alkyl of 1 to 29 carbons, CO-R$_2$, CO-O-R$_2$, CO-NH-R$_2$, or PO(OR$_2$)$_2$ or PO(OR$_2$)R$_2$, where R$_2$ independently is H, alkyl of 1 to 20 carbons, phenyl, or lower alkyl substituted phenyl or halogen substituted phenyl; A is (CH$_2$)$_n$ where n ranges between 0 to 30, or A is a a divalent branch chained alkyl radical, or cycloalkyl radical, having a total of 3 to 30 carbons; R$_3$ independently is an alkyl group having 4 to 20 carbons, and X is O or NH, have anti-inflammatory activity.

29 Claims, No Drawings

DI-(5-HYDROXY-2(5H)2-OXO-4-FURYL)ALKYL-METHYL-ALPHA,OMEGA ALKANEDIOATES AND N,N-BIS-(5-HYDROXY-2(5H)2-OXO-4-FURYL)ALKYLMETHYL-ALPHA,OMEGA-DIALKANOIC ACID AMIDES AS ANTI-INFLAMMATORY AGENTS

BACKGROUND OF THE INVENTION

1. Field of the Invention

The present invention is directed to novel substituted di-[5-hydroxy-2(5H)-4-furanonyl]alkylmethyl- alkanedioates and N,N-bis-[5-hydroxy-2(5H)-4-furanonyl]alkylmethyl- dialkanoic acid amides which are active as anti-inflammatory agents. The present invention is also directed to pharmaceutical compositions which comprises one or more of the novel compounds of the invention, to the methods of using these pharmaceutical compositions, and to the chemical processes of making the novel compounds.

2. Brief Description of the Prior Art

Manoalide is a compound isolated from a marine sponge [E. D. de Silva et al., *Tetrahedron Letters* 21:1611-1614 (1980)] which has anti-inflammatory, immunosuppressive and analgesic properties. Manoalide the structure of which is shown below, includes a 5-hydroxy-2(5H)-furanone moiety, attached in the 4-position of the furanone ring to the rest of the molecule. Certain analogs of manolide, such as seco-manoalide and dehydro-seco-manoalide also have anti-inflammatory activity. For further description of the biological activity of manoalide and some of its derivatives reference is made to U.S. Pat. Nos. 4,447,445, 4,786,651, 4,789,749 and to European Patent Application No. 0 133 376 (published on Feb. 20, 1985).

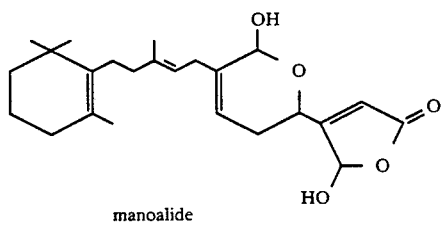

manoalide

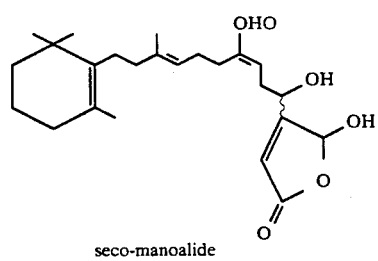

seco-manoalide

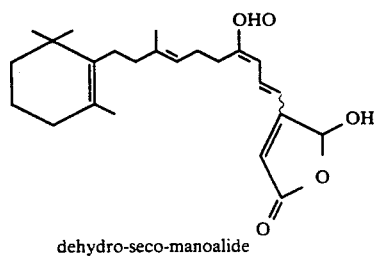

dehydro-seco-manoalide

Synthetic analogs of manoalide, particularly analogs having various substituents on the furanone moiety of manoalide, are described in patents and several applications for United States Letters Patent by the same inventor or co-inventor as in the present application, such as: U.S. Pat. Nos. 4,935,530 (issued Jun. 19, 1990), 4,957,917 (issued Sep. 18, 1990), 5,013,850 (issued May 7, 1991), 5,037,811 (issued Aug. 6, 1991) and U.S. application Ser. Nos. 699,819 (filed May 13, 1991, pending), 426,243 (filed Oct. 25, 1991, pending), 427,268 (filed Oct. 25, 1989, allowed), 510,364 (filed Apr. 17, 1990, pending), 493,895 (filed Mar. 15, 1990, allowed), 510,367, (filed Apr. 17, 1990, allowed), 693,204 (filed Apr. 30, 1991, pending) and 693,201 (filed Apr. 30, 1991, pending).

Published European Patent Application No. 0 295 056 discloses 4-substituted 5-hydroxy-2(5H)-furanones having anti-inflammatory, immunosuppressive and anti-proliferative activity where the substituents in the 4 position are a variety 1-hydroxyalkyl, 1-acyloxy-alkyl and 1-carbamoyloxy-alkyl groups.

U.S. Pat. No. 4,855,320 discloses 5-arylalkyl-4-alkoxy-2(5H)-furanones as anti-convulsive and anti-epileptic agents.

Published European Patent Application No. 0 209 274 discloses 4-alkyl-5-hydroxy-2(5H)-furanones as anti-inflammatory and anti-allergy agents.

Chemical Abstracts Volume 107 236559t (1987) discloses 4-acyloxy 5-hydroxy-2(5H)-furanones.

SUMMARY OF THE INVENTION

The present invention covers compounds of Formula 1,

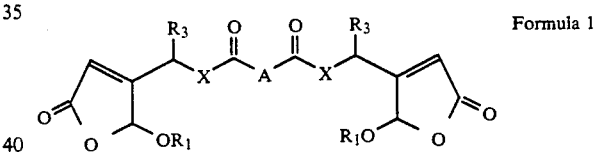

Formula 1 in Which $R_1$ independently is H or alkyl of 1 to 20 carbons, $CO-R_2$, $CO-O-R_2$, $CO-NH-R_2$, or $PO(OR_2)_2$ or $PO(OR_2)R_2$, where $R_2$ independently is H, alkyl of 1 to 20 carbons, phenyl, or lower alkyl substituted phenyl or halogen substituted phenyl;

A is $(CH_2)_n$ where n ranges between 0 to 30, or A is a a divalent branch chained alkyl radical, or cycloalkyl radical, having a total of 3 to 30 carbons;

$R_3$ independently is an alkyl group having 4 to 20 carbons, and

X is O or NH.

The present invention also covers salts of the above-defined compounds, formed with pharmaceutically acceptable acids or bases, as applicable.

In a second aspect, the present invention relates to pharmaceutical formulations comprising one or more compounds of Formula 1 (or pharmaceutically acceptable salts thereof) in admixture with a pharmaceutically acceptable excipient, for the purpose of treating certain conditions, syndromes or diseases in mammals, including humans. The compounds of the invention have anti-inflammatory, immunosuppressant and anti-proliferative activity. Therefore, the compounds are useful for treating in mammals (including humans) inflammation, rheumatoid arthritis, osteoarthritis, rheumatic carditis, ocular and dermal inflammatory diseases, autoimmune diseases such as allergic diseases, bronchial asthma and myasthenia gravis, and for suppressing unwanted immune responses and retarding proliferation of cell.

In still another aspect, the present invention relates to processes of making the compounds of Formula 1. In general terms, these processes, shown in a summarized fashion in Reaction Scheme 1 for the compounds of the invention where in Formula 1 X is O, comprise the steps can be halogen, chlorine, bromine or iodine or other leaving group. Generally speaking, such reaction conditions are employed for the reaction between the compounds of Formula 3 and Formula 4 which are generally known in the art to effectuate the formation of ester linkages. L may even be OH, and the reaction may be conducted in the presence of dicyclohexyldiimide (DCC).

REACTION SCHEME 1

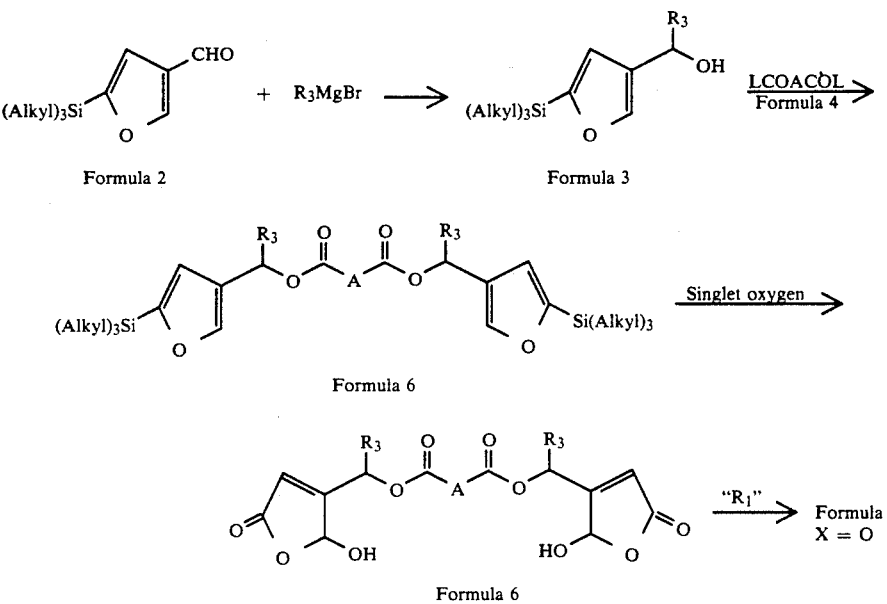

of reacting a 2-trialkylsilyl-4-furaldehyde of Formula 2 with a Grignard (or like) reagent having the structure $R_3$-MgBr (where $R_3$ is defined as in connection with Formula 1) to yield a 2-trialkylsilyl-4-(1-hydroxy)alkyl-furan of Formula 3. The 2-trialkylsilyl-4-(1-hydroxy)alkyl-furan of Formula 3 is then reacted With a suitable derivative of a dicarboxylic acid of the general Formula 4, to provide a compound of general Formula 5, where the CO—A—CO group derived from the dicarboxylic acid links the two (2-trialkylsily-4-furyl)(1-hydroxy)-methyl groups with "ester" linkages, to form compounds of Formula 5. The group L in general Formula 4 represents a group suitable for activating the dicarboxylic acid to form the ester linkages. Accordingly L The compounds of Formula 5 are converted into the compounds of Formula 6 by exposure to singlet oxygen. As is described below in more detail and is specifically illustrated in the appended examples, reaction of the herein-described furane derivatives with singlet oxygen involves irradiation of the furane derivative of Formula 6 in the presence of oxygen in a suitable solvent. The compounds of Formula 6 are compounds of the invention, where, with reference to Formula 1 X is O and $R_1$ is H. The compounds of Formula 1 where $R_1$ is other than hydrogen can be obtained from the compounds of Formula 5 by alkylation, acylation, or other reactions (which per se are well known in the art) to introduce the $R_1$ substituent.

REACTION SCHEME 2

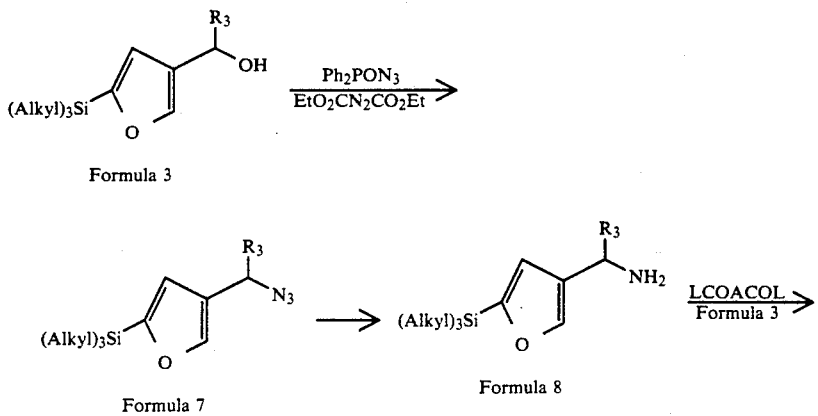

REACTION SCHEME 2
-continued

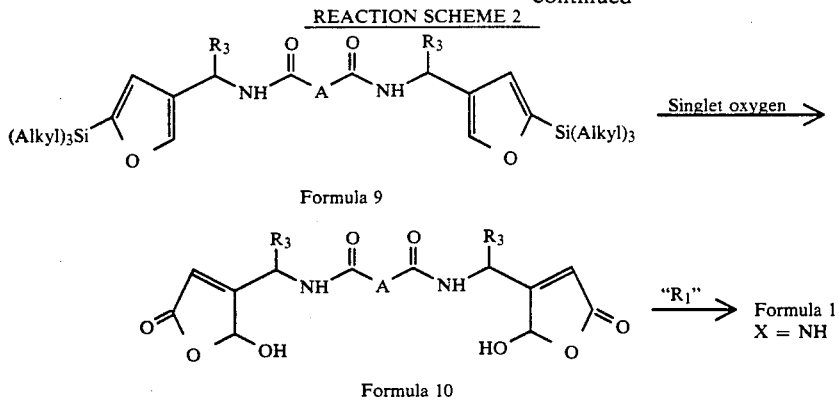

Formula 9

Formula 10

Referring now to Reaction Scheme 2, the compounds of the invention where, with reference to Formula 1 X is NH, are prepared by first converting the intermediate 2-trialkylsilyl-4-(1-hydroxy)alkyl-furans of Formula 3 to 2-trialkylsilyl-4-1-amino)alkyl-furans of Formula 8. This is best accomplished by reacting the compounds of Formula 3 with diphenylphosphorylazide ($Ph_2PON_3$) in the presence of diethyl azidocarboxylate (EtOOC-NN-COOEt) to provide the 2-trialkylsilyl-4-(1-azido)alkyl-furans of Formula 7, which are subsequently reduced (with lithium aluminum hydride) to yield the compounds of Formula 8. The 2-trialkylsilyl-4-(1-amino)alkyl-furans of Formula 8 are then reacted with the dicarboxylic acid derivative of Formula 4, to provide a compound of general Formula 9, where the CO—A—CO group derived from the dicarboxylic acid links the two (2-trialkylsily-4-furyl)(1-amino)methyl groups with "amide" linkages, to form the compounds of Formula 9. The group L of the compounds of Formula 4 can be characterized in substantially the same manner as in connection with Reaction Scheme 1. In other words, L represents a group suitable for activating the dicarboxylic acid to form the amide linkages and, generally speaking, such reaction conditions are employed for the reaction between the compounds of Formula 8 and Formula 4 which are generally known in the art to effectuate the formation of amide linkages. The N,N-bis-[2-trialkylsilyl-4-furyl]alkylmethyl- dialkanoic acid amide compounds of Formula 9 are converted to the compounds of Formula 10 by oxidation with singlet oxygen. The compounds of Formula 10 are compounds of the invention where, with reference to Formula 1, X is NH and $R_1$ is H. The compounds of Formula 1 where $R_1$ is other than hydrogen, can be obtained from the compounds of Formula 10 by alkylation, acylation, or other reactions (which per se are well known in the art) to introduce the $R_1$ substituent.

GENERAL EMBODIMENTS

Definitions

The terms "ester", "amine", "amide", and all other terms and terminology used here, (unless specifically defined in the present description) refer to and cover any compounds falling within the respective term as that term is classically used in organic chemistry.

The term "alkyl" as used in the present description and claims includes straight chain alkyl groups, branched chain alkyl groups, cycloalkyl groups, alkyl substituted cycloalkyl groups, and cycloalkyl substituted alkyl groups. Unless the number of carbons is otherwise specified, "lower alkyl" means the former broad definition of "alkyl" groups but with the restriction that the group has 1 to 6 carbon atoms.

Some of the compounds of the invention may contain a chiral center. Other compounds of the invention may contain more than one chiral center. Accordingly, the compounds of the invention may be prepared as mixtures of enantiomeric compounds (where the enatiomers may or may not be present in equal amounts) or as optically pure enantiomers. When there is more than one chiral center, the compounds of the invention may also be prepared as mixtures of diastereomers, or as pure diastereomers, and each diastereomer itself may be a mixture of enantiomers in 1:1, or other, ratios. Alternatively, each diastereomeric compound may be sterically and optically pure. However, all of the above-noted forms, including optically pure enantiomers and mixtures thereof, as well as all diastereomers, are within the scope of the present invention.

Some of the compounds of the invention may have cis and trans stereoisomers. The scope of the invention includes both pure stereoisomers as well as mixtures thereof.

A pharmaceutically acceptable salt may be prepared for any compound of this invention having a functionality capable of forming such salt, for example an acid or an amine functionality. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

The preferred compounds of the present invention are, with reference to Formula 1 and with respect to the 5-position of the furanone moiety, those where the substituent is hydroxy ($R_1$ is H) or acetoxy ($R_1$ is $COCH_3$).

With reference to the length of the alkyl chain (A) in the dicarboxylic acid residue (CO—A—CO) which connects the two (5-hydroxy-2(5H)-furano-yl)(1-hydroxy)alkyl or the two (5-hydroxy-2(5H)-furano-yl)(1-amino)alkyl moieties of the compounds of the present invention, the alkyl chain may contain between approximately 0 to 30 carbons; preferrably A is a straight chain divalent alkyl radical represented by $(CH_2)_n$ where n is an integer between 0 to 30, more preferably between 0 to 16.

With reference to the alkyl substituent on the alpha carbon in the 4-position of the furan nucleus of the compounds of the present invention ($R_3$ in Formula 1), the alkyl substituent may contain 5 to 20 carbons. Preferably the alkyl substituent ($R_3$) is n-alkyl, having 6 to 16 carbons.

The most preferred compounds of the invention are listed below with reference to Formula 11:

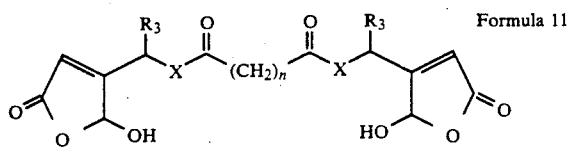

Formula 11

Compound 1: X=O, n=1, $R_3$=—$(CH_2)_{11}CH_3$;
Compound 2: X=O, n=3, $R_3$=—$(CH_2)_{11}CH_3$;
Compound 3: X=NH, n=3, $R_3$=—$(CH_2)_{11}CH_3$;
Compound 4: X=O, n=1, $R_3$=—$(CH_2)_5CH_3$;

The compounds of the present invention are useful in pharmaceutical compositions to produce anti-inflammatory, immunosuppressant and anti-proliferative activity. The diseases, syndromes or conditions of mammals (including humans) which can be treated with pharmaceutical compositions containing one or more compounds of the invention (or salts thereof) include: inflammation, rheumatoid arthritis, osteoarthritis, rheumatic carditis, ocular and dermal inflammatory diseases, autoimmune diseases such as allergic diseases, bronchial asthma and myasthenia gravis, unwanted immune responses and unwanted proliferation of cells, psoriasis, acne, atopic diseases and allergic conjunctivitis.

The activity of the compounds of this invention is demonstrated by inhibition of the enzyme phospholipase $A_2$ in vitro and by reduction of inflammation in the mouse ear anti-inflammatory assay in vivo.

Activity of compounds of this invention may also be demonstrated by inhibition of phosphoinositide-specific phospholipase C. This activity has been reported for manoalide and may indicate anti-inflammatory utility. Bennett et al, *Molecular Pharmacology* 32:587–593 (1987).

Activity of the compounds may also be demonstrated by inhibition of ornithine decarboxylase, a rate limiting enzyme in cellular growth, which indicates use in treating psoriasis and neoplasis.

The compounds also modify calcium homeostasis. This activity is shown by effect on intracellular calcium levels in experiments using gastric glands, spleen cells, epithelial cells, $GH_3$ cells, etc. Calcium is inhibited from entering through the plasma membrane calcium channels and calcium release from intracellular stores is also blocked. Modification of calcium homeostasis is expected to have application in diseases of the nervous system involving modification of membrane lipids or transmitter release (Parkinson's, Alzheimer's), diseases of the cardiovascular system involving application of cardiac or vascular smooth muscle contractility and platelet aggregation (hypertension, cardiac infarction and atherosclerosis), diseases of the gastrointestinal tract such as ulcer disease, diarrhea, motility due to secretion of acid or $Cl^-$, diseases of the kidney involving renal handling of fluid and electrolytes (metabolic acidosis, alkalosis), and disease of abnormal growth (neoplasia, psoriasis).

The compounds of this invention have activity which is similar to that of manoalide, that is the compounds appear to be devoid of the endocrine properties of the glucocorticoids while having anti-inflammatory and immunosuppressive properties.

In the methods of this invention, the compounds of the invention are administered to mammals, including humans, in an effective amount to produce the desired activity, preferably in an amount of about 0.05 to 100 mg per day per kilogram of body weight. The amount of the compound depends upon the disease or condition being treated, the severity thereof, the route of administration and the nature of the host. The compounds may be administered topically, orally, parenterally or by other standard routes of administration.

Pharmaceutical compositions of this invention comprise compounds of Formula 1, and pharmaceutical carriers suitable for the route of administration. Standard methods for formulating pharmaceutical compositions of this type may be found in *Remington's Pharmaceutical Sciences*, Mack Publishing Company, Easton, Pa.

For topical administration, the pharmaceutical composition may be in the form of a salve, cream, ointment, spray, powder or the like. Standard pharmaceutical carriers for such compositions may be used. Preferably, compositions for topical administration will contain 0.05–5% of the active ingredient.

A typical cream formulation may contain the following:

| Ingredient | Parts by Weight |
| --- | --- |
| Water/glycol mixture (15% or more glycol) | 50–99 |
| Fatty alcohol | 1–20 |
| Non-ionic surfactant | 0–10 |
| Mineral oil | 0–10 |
| Typical pharmaceutical adjuvants | 0–5 |
| Active ingredient | 0.05–5 |

A typical ointment formulation may contain the following:

| Ingredients | Parts by Weight |
| --- | --- |
| White petrolatum | 40–94 |
| Mineral oil | 5–20 |
| Glycol solvent | 1–15 |
| Surfactant | 0–10 |
| Stabilizer | 0–10 |
| Active ingredient | 0.05–5 |

For oral administration, suitable pharmaceutical carriers include mannitol, lactose, starch, magnesium stearate, talcum, glucose and magnesium carbonate. Oral compositions may be in the form of tablets, capsules, powders, solutions, suspensions, sustained release formulations, and the like.

A typical tablet or capsule may contain the following:

| Ingredients | Percent w/w |
| --- | --- |
| Lactose, spray-dried | 40-99 |
| Magnesium stearate | 1-2 |
| Cornstarch | 10-20 |
| Active ingredient | 0.001-20 |

Parenteral compositions are prepared in conventional suspension or solution forms, as emulsions or as solid forms for reconstruction. Suitable carriers are water, saline, dextrose, Hank's solution, Ringer's solution, glycerol, and the like. Parenteral administration is usually by injection which may be subcutaneous, intramuscular or intravenous.

The compounds of this invention may be combined with other known anti-inflammatory/immunosuppressive agents such as steroids or non-steroidal anti-inflammatory agents (NSAID) in the pharmaceutical compositions and methods described herein.

The assay procedures by which useful biological activity of the compounds of the invention can be demonstrated, are described below.

Calcium Channel (mobilization) Inhibition Assay

Polymorphonuclear leukocytes (PMNa), gastric glands, GH$_3$ cells, A431 cells, spleen cells, human keratinocytes corneal cells, etc. were loaded with the Ca$^{2+}$ sensitive fluorescent dye, Fura-2. The appropriate cell type was chosen and the potency and efficacy of the anti-inflammatory furanones on calcium mobilization, calcium channel inhibition was quantitated. The methods used for A431 cells listed below are representative of those used for other cells.

A431 cells were detached using a 5-10 min trypsin-EDTA treatment whereas GH$_3$ cells were treated 2 to 5 min with a 1% pancreatin solution. Cells were immediately washed twice in a 20 mM HEPES buffer (pH 7.4) containing 120 mM NaCl, 6 mM KCl, 1 mM MgSO$_4$, 1 mg/ml glucose and 1 mg/ml pyruvate and 1.4 mM calcium (medium A). Approximately $5 \times 10^6$ cells were suspended in medium A and incubated with 4 uM fura-2-AM for 15 min at 37° C.

After washing the fura-2 loaded cells, the uptake of dye was checked using fluorescence microscopy and found to be evenly distributed in the cytosol of all cells. Fluorescence was continuously recorded with a Perkin-Elmer LS-5 spectrofluorometer. The excitation wavelength was set at 340 nm and emission wavelength set at 500 nm. The cell suspension was continually stirred, maintained at 37° C. and equilibrated for approximately 5 min before addition of various agents. [Ca$^{2+}$]i was calculated using the following formula:

$$[Ca^{2+}]_i = 220 \times \frac{F - F_{min}}{F_{max} - F}$$

All fluorescence values were measured relative to a EGTA-quenched signal determined as follows: F was the relative fluorescence measurement of the sample. $F_{max}$ was determined by lysing the cells with digitonin (1000 ug/ml) in DMSO. After $F_{max}$ was determined the pH was adjusted to 8, with NaOH and Ca$^{2+}$ chelated with 3 mM EGTA to totally quench the fura-2 signal and obtain $F_{min}$.

When quin-2- was used, cells were incubated with 10 uM quin-2- at 37° C. for 1 hour, washed and then used.

Mouse Ear Anti-Inflammatory Assay

Test compound and phorbol myristate acetate (PMA) are topically applied simultaneously to the pinnae of the left ears of mice. PMA alone is applied to the right ear. Three hours and 20 minutes after application, the mice are sacrificed, left and right ears removed, and standard sized bores taken. Edema (inflammation) is measured as the difference in weight between left and right ears [Van Arman, C. G., Clin Pharmacol Ther (1974) 16:900-904].

Inhibition of Phospholipase A$_2$

The effect of compounds of this invention on bee venom phospholipase A$_2$ is determined by the following procedure:

a. Bee venom phospholipase A$_2$ in 10 uM HEPES (pH 7.4) with 1 mM CaCl$_2$ is incubated with vehicle or test agent for 1.0 hour at 41°.

b. 1.36 mM phosphotidylcholine, 2.76 mM Triton X-100 are dispersed in buffer by sonication and then mixed with L-3 phosphotidylcholine, 1-palmitoyl-2-(1-$^{14}$C) palmitoyl for 10 min.

c. Start the reaction by the addition of enzyme (0.495 units/ml).

d. Incubation for 15 sec. at 41°.

e. Reaction is terminated by addition of 2.5 ml of isopropanol: n-heptane: 0.5M H$_2$SO$_4$ (40:10:1; v:v:v:).

f. 2.0 ml n-heptane and 1.0 ml H$_2$O added; mixture centrifuged.

g. 2.0 ml n-heptane removed and treated with 200-300 mg of silica gel HR60.

h. Samples centrifuged; 1 ml of n-heptane SN removed and added to 10 ml scintillation fluid.

i. Samples counted on a scintillation counter.

Inhibition of Phosphoinositide-specific Phospholipase C

The effect of compounds of this invention on phosphoinositide-specific phospholipase C may be determined by procedures described by Bennett et al, *Molecular Pharmacology* 32:587-593 (1987).

Activity Data

In the above-described phospholipase A$_2$ (PLA$_2$) and phosphoinositide-specific phospholipase C (PLC) assays Compound 1 of the present invention was found to provide 50% inhibition (IC$_{50}$) of the respective venom phospholipase enzymes at the following concentrations (in micromoles), as indicated in Table 1.

TABLE 1

| | PLA$_2$ | PLC |
| --- | --- | --- |
| Compound name or number | IC$_{50}$ (um) | IC$_{50}$ (um) |
| 1 | 0.02 | 2 |
| 2 | 0.03 | — |
| 4 | 0.03 | — |
| manoalide* | 0.03 | 3 |

*Data for monoalide are provided for comparison.

Specific Embodiments

The compounds of the present invention can be made by the synthetic chemical pathways which were described above in general terms, and specifically illustrated in the specific examples below. The synthetic chemist will readily appreciate that the conditions described here in general terms, and specifically, can be generalized to any and all compounds represented by Formula 1. Furthermore, the synthetic chemist will readily appreciate that the herein described synthetic steps may be varied or adjusted by those skilled in the art without departing from the scope and spirit of the invention.

The starting compounds for the synthesis of the compounds of the present invention are the 2-trialkylsilyl-4-furaldehydes (Formula 2) preferably 2-trimethylsilyl-4-furaldehyde (Compound 5) and most preferably 2-triethylsilyl-4-furaldehyde (Compound 6). The compounds of Formula 2 can be synthesized from commercially available 3-furaldehyde, in the manner described below and also in co-pending application Ser. No. 07/690,444 filed on Apr. 24, 1991, which has been allowed and is expected to issue as a United States patent. The specification of allowed application Ser. No. 07/690,444 is hereby expressly incorporated by reference.

With regard to the reaction step of exposing the intermediate compounds of Formula 5 and Formula 9 to the action of singlet oxygen, the following is noted. The conditions of these reactions are described in detail in connection with the specific examples. In general terms, the reactions are conducted in a mixture of water and acetone or in a mixture of water and tetrahydrofuran, and in some instances in substantially neat tetrahydrofuran, in the presence of an initiator, preferably Rose Bengal dye (preferably polymer bounded), which is added to the reaction mixture. The reaction mixture and vessel is flushed with oxygen and the reaction is conducted at low temperature, at approximately $-78°$ C., or for the herein described reactions preferably at approximately $0°$ C., under a constant positive pressure of oxygen for a number of hours, typically 1 to 7 hours. The mixture is typically irradiated with a 150 Watt flood lamp. Work-up of the reaction mixture after irradiation usually includes concentration by evaporation of the solvent, followed by chromatography on silica gel, in columns or on preparative silica plates.

The following examples of specific compounds of the invention, and specific examples of the synthetic steps in which the compounds and certain intermediates are made, are set out to illustrate the invention, not to limit its scope.

2-Trimethylsilyl-4-furaldehyde

Compound 5 n-Butyl lithium (a 2.5M solution in hexane; 28.8 ml, 72 mmol) was added to a solution of morpholine (6.28 ml, 72 mmol) in tetrahydrofuran (700 ml) at $-78°$ under argon. After 20 minutes, 3-furaldehyde (7.0 g, 72 mmol) was added. After another 20 minutes, sec-butyl lithium (a 1.3M solution in cyclohexane; 55.4 ml, 72 mmol) was added dropwise and stirring continued at $-78°$ for 7 hours before trimethylsilyl chloride (27 ml, 216 mmol) was added. Stirring was continued overnight (14 hours) while the cooling bath was allowed to attain room temperature. The solution was poured into ice cold 10% (v/v) hydrochloric acid (200 ml) and after stirring at $0°$ for 10 minutes, the layers were separated. The aqueous phase was extracted with diethyl ether. All the organic phases were combined, dried (magnesium sulfate) and evaporated to dryness to give a light brown oil, which was purified by flash chromatography on silica using 2% ethyl ether/hexane. Fractions with $R_f$ of about 0.30 (silica, 10% ethyl ether/hexane) on evaporation gave the title aldehyde as a light yellow oil, b.p. $48°-50°/0.25$ torr.

$^1$H NMR (CDCl$_3$) 0.29 (s, 9H), 6.98 (s, 1H), 8.25 (s, 1H) and 9.95 (s, 1H).

$^{13}$C NMR (CDCl$_3$) $-2.0$, 116.2, 128.9, 155.3, 164.1 and 184.5.

HRMS exact mass calculated for C$_8$H$_{12}$O$_2$Si(M$^+$) 168.0607, found 168.0588. See also U.S. Pat. No. 4,935,530, the specification of which is incorporated herein by reference.

2-Triethylsilyl-4-furaldehyde

Compound 6 n-Butyl lithium (a 2.5M solution in hexane; 30.6 ml, 76.5 mmol) was added to a solution of morpholine (6.66 ml, 76.5 mmol) in tetrahydrofuran (500 ml) at $-78°$ under argon. After 15 minutes, 3-furaldehyde (6.3 ml, 72.8 mmol) was added. After another 20 minutes, sec-butyl lithium (a 1.3M solution cyclo-hexane; 59.0 ml, 76.5 mmol) was added dropwise and stirring continued at $-78°$ for about 2 hours before triethylsilylchloride (13.4 ml, 80.1 mmol) was added. Stirring was continued overnight (14 hours) while the cooling bath was allowed to attain room temperature. The solution was poured into ice cold 10% (v/v) hydrochloric acid (100 ml) and another stirring at $0°$ for 10 minutes, the layers were separated. The aqueous phase was extracted with diethyl ether. All the organic phases were combined, dried (magnesium sulfate) and evaporated down to give an oil, which was distilled under high vacuum to give the 5-triethylsily-3-furaldehyde as a pale yellow oil, boiling point $85°-90°/0.4$ torr.

IR (neat) 1680 cm$^{-1}$ $^1$H NMR (CDCl$_3$) 0.79 (q, 6H, J=7.3 Hz), 0.90 (t, 9H, J=7.3 Hz), 7.0 (s, 1H), 8.26 (s, 1H) and 9.95 (s, 1H).

$^{13}$C NMR (CDCL$_3$) 2.9, 7.1, 117.2, 128.8, 155.6, 162.3 and 184.6.

HRMS m/e exact mass calculated for C$_{11}$H$_{18}$O$_2$Si(M$^+$) 210.1076, found 210.1071.

4-(1-Hydroxytridecyl)-2-triethylsilylfuran

Compound 7

Dodecylmagnesium bromide (a 1M solution in tetrahydrofuran; 14.3 ml; 14.3 mmol) was added dropwise to a solution of 2-triethylsilyl-4-furaldehyde (Compound 6, 2.0 g, 9.52 mmol) in THF (20 ml) at 0 degrees C. under argon. After stirring at room temperature for 2 hours, the mixture was quenched with dilute HCl and extracted with ethyl ether. Evaporation of the dried (magnesium sulfate) extracts gave an oil, which was purified by flash chromatography on silica using 30% ethyl ether/hexane to give the titled alcohol. $^1$HNMR (CDCl$_3$) 0.76 (q, 6H, J=8.0 Hz), 0.88 (t, 3H, J=6.3 Hz), 0.98 (t, 9H, J=8.0 Hz), 1.25 (m, 20H), 1.62 (d, 1H, J=4.3 Hz), 1.75 (m, 2H), 4.63 (dd, 1H, J=6.6 Hz, 1.9 Hz), 6.63 (s, 1H) and 7.57 (s, 1H).

Bis[1-(2-triethylsilyl-4-furyl)tridecyl] malonate

Compound 8

Malonyl dichloride (49 microliter, 0.5 mmol) was added dropwise to a solution of 4-(1-hydroxytridecyl)-2-triethylsilylfuran (Compound 7, 0.40 g, 1.05 mmol) at 0 degrees C. After 5 minutes, diisopropylethylamine (0.17 ml, 1.0 mmol) was added and stirring was continued at 0 degrees C. for 3 hours. The mixture was quenched with water and extracted with (ethyl ether). Evaporation of the dried (magnesium sulfate) extracts gave an oil, which was purified by flash chromatography on silica using 7.5% ethyl ether/hexane to give the titled ester.

¹HNMR (CDCl₃) 0.76 (q, 12H, J=8.0 Hz), 0.88 (t, 6H, J=6.9 Hz), 0.97 (t, 18H, J=8.0 Hz), 1.25 (m, 40H), 1.80 (m, 4H), 3.36 (s, 2H), 5.82 (t, 2H, J=6.6 Hz), 6.58 (s, 2H) and 7.60 (s, 2H).

¹³C NMR (CDCl₃) 2.9, 7.0, 13.8, 22.5, 25.2, 29.0, 29.2, 29.3, 29.4, 29.5, 31.7, 34.4, 42.0, 69.9, 119.7, 124.4, 144.9, 159.6 and 166.3

LRMS (FAB) 851.6 (M+Na⁺).

Bis[1-(5-hydroxy-2(5H)-furano-4-yl)tridecyl]malonate

Compound 1

A mixture of bis[1-(2-triethylsilyl-4-furyl)tridecyl]-malonate (Compound 8, 226 mg, 0.27 mmol), Rose Bengal (5 mg) and water (1 ml) in acetone (20 ml) was exposed to singlet oxygen at 0 degrees C. for 7 hours. On evaporation, the residue was purified by flash chromatography on silica using 40% ethyl acetate/hexane to give the titled furanone.

IR (CHCl₃) 3400 and 1765.

¹HNMR (CDCl₃) 0.68 (t, 6H, J=7.0 Hz), 1.26 (m, 40H), 1.85 (br, 4H), 3.56 (br, 2H), 5.68 (br, 1H), 5.76 (br, 1H), 6.04 (s, 2H), 6.06 (s, 1H) and 6.25 (brs, 1H).

¹³C NMR (CDCl₃) 13.8, 22.4, 24.7, 28.9, 29.1, 29.2, 29.3, 29.4, 31.7, 32.6, 40.6, 40.8, 70.4, 70.5, 71.2, 98.1, 118.8, 119.8, 119.9, 165.8, 166.3 and 171.0.

HRMS (FAB) exact mass calculated for C₃₇H₆₀O₁₀Na 687.4084, found 687.4091.

Di[1-(2-triethylsilyl-4-furyl)]tridecyl 1,5-pentandioate

Compound 9 n-Dodecylmagnesium bromide (a 1.0M solution in THF; 7.52 ml; 7.52 mmol) was added to a solution of 2-triethylsilyl-4-furaldehyde (Compound 6, 1.58 g, 7.52 mmol) in THF (20 ml) at 0 degrees C. under argon. The mixture was warmed to room temperature. When all the aldehyde was consumed, as shown by TLC, the mixture was recooled to 0 degrees C. and 1,5-pentandioyl chloride (0.44 ml, 3.42 mmol) was added. Stirring was continued at room temperature overnight and the mixture was quenched with 5% ammonium chloride solution. Extraction (ethyl ether) and evaporation of the dried (magnesium sulfate) extracts gave an oil. The crude product was purified by flash chromatography (SiO₂, 5% ethyl ether/hexane) to give the titled furan.

IR (CHCl₃) 1725;

¹HNMR (CDCl₃) 0.75, (q, 12H, J=7.5 Hz), 0.88 (t, 6H, J=6.9 Hz), 0.94 (t, 18H, J=7.5 Hz), 1.25 (brs, 40H), 1.80 (m, 4H), 1.95 (p, 2H, J=6.2 Hz), 2.33 (t, 4H, J=6.2 Hz), 5.80 (t, 2H, J=7.5 Hz), 6.58 (s, 2H) and 7.59 (s, 2H).

¹³C NMR (CDCl₁₃) 2.89, 6.99, 13.8, 20.1, 22.5, 25.3, 29.1, 29.2, 29.3, 29.4, 31.7, 33.4, 34.6, 68.6, 119.7, 124.9, 144.7, 159.5 and 172.7.

4-(1-Azidotridecyl)-2-triethylsilylfuran

Compound 10

A solution of diphenylphosphorylazide (143 mg, 0.52 mmol) in THF (2 ml) was added over a period of 15 minutes to a solution of 4-(1-hydroxytridecyl)-2-triethylsilylfuran (Compound 7, 200 mg, 0.52 mmol), triphenylphosphine (140 mg, 0.52 mmol) and diethyl azidocarboxylate (90 mg, 0.52 mmol) in THF (10 ml) at room temperature. After stirring for 2 days, the mixture was evaporated in the presence of a minimum amount of silica gel. The residue was purified by flash chromatography on silica using 5% ethyl ether/hexane to give the titled azide.

¹HNMR (CDCl₃) 0.77 (q, 6H, J=8.0 Hz), 0.88 (t, 3H, J=6.4 Hz), 0.98 (t, 9H, J=8.0 Hz), 1.25 (m, 20H), 1.75 (m, 2H), 4.33 (t, 1H, J=7.5 Hz), 6.60 (s, 1H) and 7.61 (s, 1H).

4-(1—Aminotridecyl)-2-triethylsilylfuran

Compound 11

A solution of lithium aluminum hydride (a 1.0M solution in THF; 4.22 ml, 4.22 mmol) was added slowly to a solution of 4-(1-azidotridecyl)-2-triethylsilylfuran (Compound 10, 1.55 g, 3.84 mmol) at 0 degrees C. under argon. After stirring at room temperature for 2 hours, the mixture was cooled to 0 degrees C. and quenched with 2M sodium hydroxide. Anhydrous sodium sulfate was added to coagulate the aluminum salt and the mixture was extracted thoroughly with ethyl acetate. Evaporation of the dried (magnesium sulfate) extracts gave an oil, which was purified by flash chromatography on silica using 5% methanol/dichloromethane to give the titled amine.

¹H NMR (CDCl₃) 0.76 (q, 6H, J=8.0 Hz), 0.88 (t, 3H, J=6.5 Hz), 0.98 (t, 9H, J=8.0 Hz), 1.25 (m, 20H), 1.80 (m, 2H), 3.85 (t, 1H, J=6.8 Hz), 6.60 (s, 1H) and 7.50 (s, 1H).

N,N'-bis[2-triethylsilyl-4-furyl)tridecyl]-1,5-pentadiamide

Compound 12

1,5-Pentanoyl dichloride (50 microliter, 0.39 mmol), followed by triethylamine (0.11 ml, 0.79 mmol) was added to a solution of 4-(1-aminotridecyl)-2-triethylsilylfuran (Compound 11, 142 mg, 0.38 mmol) in dichloromethane at room temperature. After stirring for 15 hours, the mixture was quenched with water and extracted with ethyl ether. Evaporation of the dried (magnesium sulfate) extracts gave an oil, which was purified by flash chromatography to give the titled amide. R$_f$ (50% ethyl ether/hexane) 0.09.

¹H NMR (CDCl₃) 0.74 (q, 12H, J=7.9 Hz) 0.89 (t, 6H, J=6.8 Hz), 0.98 (q, 18H, J=7.9 Hz), 1.26 (brs, 40H), 1.70 (brm, 4H), 2.0 (m, 2H), 2.25 (m, 4H), 5.0 (q, 2H, J=7.5 Hz), 5.58 (m, 2H), 6.55 (s, 2H), 7.53 (s, 1H) and 7.54 (s, 1H).

N,N'-bis[1-(5-hydroxy-2(5H)2-oxo-4-furyl)tridecyl]-1,5-pentadiamide

Compound 3

Singlet oxygen oxidation of N,N'-bis[triethylsilyl-4-furyl)tridecyl]-1,5-pentadiamide (compound 12), under the usual condition, gave the titled furanone.

Di[1-(5-hydroxy-2(5H)2-oxo-4-furyl]tridecyl 1,5-pentandioate

Compound 2

A mixture of di-[1-(2-triethylsilyl-4-furyl)]tridecyl 1,5-pentandioate (Compound 9, 1.98 g, 2.32 mmol), Rose Bengal (ca, 5 mg) and water (2 ml) in THF (150 ml) was exposed to singlet oxygen at 0 degrees C. for 7 hours. The residue, after evaporation, was purified by flash chromatography (SiO₂, 30% ethyl acetate/hexane) to give the titled furanone.

IR (CHCl₃) 3500-3300, 1750;

1HNMR (CDCl3) 6.89 (t, 6H, J=6.8 Hz), 1.27 (brm, 40H), 1.83 (m, 4H), 1.99 (m, 2H), 2.48 (t, 4H, J=6.9 Hz), 5.57 (t, 2H, J=6.2 Hz), 5.85 (br, 2H), 6.00 (s, 1H), 6.02 (s, 1H) and 6.15 (br, 2H).

13C NMR (CDCl3) 13.8, 19.4, 19.6, 22.5, 24.9, 29.0, 29.1, 29.2, 29.4, 29.5, 31.8, 32.8, 32.9, 69.7, 98.4, 118.9, 119.0, 119.1, 119.3, 166.9, 167.0, 170.8, 170.9 and 173.1.

Di-[(1-2-triethylsilyl-4-furyl)heptyl]malonate

Compound 13

Using the same procedure as for di[1-2(triethylsilyl-4-furyl)]-tridecyl 1,5-pentandioate (Compound 9), except using hexyl magnesium bromide and malonyl dichloride instead of dodecylmagnesium bromide and 1,5-pentanoyl dichloride respectively, the title compound was obtained.

IR (CHCl3) 1740, 1725.

1H NMR (CDCl3) 0.77 (q, 12H, J=7.5 Hz), 0.87 (t, 6H, J=6.8 Hz), 0.96 (t, 18H, J=7.5 Hz), 1.26 (brs, 20H), 3.56 (s, 2H), 5.83 (t, 2H, J=7.4 Hz), 6.58 (s, 2H) and 7.59 (s, 2H).

13C NMR (CDCl3) 2.89, 6.98, 13.7, 22.3, 25.1, 28.7, 31.4, 34.4, 41.9, 69.9, 119.7, 124.5, 144.9, 159.6 and 166.3.

Di[(1-5-hydroxy-2(5H)2-oxo-4-furyl)heptyl]malonate

Compound 4

A mixture of di-[(1-2-triethylsilyl-4-furyl)heptyl] malonate (Compound 13, 680 mg, 1.37 mmol) Rose Bengal (ca, 5 mg) and water (1 ml) in acetone (100 ml) was exposed to singlet oxygen at 0 degrees C. for 7 hours. The residue, after evaporation, was purified by flash chromatography (SiO2, 30% ethyl acetate/hexane) to give the title furanone.

IR (CHCl3) 3500-3300, 1800-1720

1H NMR (CDCl3) 0.88 (t, 6H, J=6.9 Hz), 1.25 (brm, 12H), 1.83 (m, 4H), 3.53 (brm, 2H), 5.25 (br, 2H), 5.65 (t, 2H, J=5.9 Hz) and 6.06 (brs, 4H).

13C NMR (CDCl3) 13.7, 22.3, 24.6, 28.5, 31.3, 32.5, 40.7, 40.8, 60.5, 70.6, 70.7, 70.8, 70.9, (br), 98.2, 118.8, 118.9, 119.0, 119.7, 166.2 and 170.9.

What is claimed is:

1. A compound of the formula

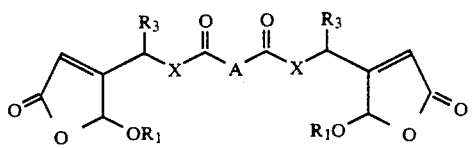

wherein
$R_1$ independently is H or alkyl of 1 to 20 carbons, $CO-R_2$, $CO-O-R_2$, $CO-NH-R_2$, or $PO(OR_2)_2$ or $PO(OR_2)R_2$, where $R_2$ independently is H, alkyl of 1 to 20 carbons, phenyl, or lower alkyl substituted phenyl or halogen substituted phenyl;
A is $(CH_2)_n$ where n ranges between 0 to 30, or A is a a divalent branch chained alkyl radical, or cycloalkyl radical, having a total of 3 to 30 carbons;
$R_3$ independently is an alkyl group having 4 to 20 carbons, and
X is O or NH, or a pharmaceutically acceptable salt thereof.

2. A compound of claim 1 wherein X is O.
3. A compound of claim 2 wherein $R_1$ is H.
4. A compound of claim 2 wherein $R_1$ is $CH_3CO$.
5. A compound of claim 2 wherein A is $(CH_2)_n$.
6. A compound of claim 2 wherein $R_3$ is normal-alkyl.
7. A compound of claim 1 wherein X is NH.
8. A compound of claim 7 wherein $R_1$ is H.
9. A compound of claim 7 wherein $R_1$ is $CH_3CO$.
10. A compound of claim 7 wherein A is $(CH_2)_n$.
11. A compound of claim 7 wherein $R_3$ is normal-alkyl.
12. A pharmaceutical composition for the treatment of a mammal comprising a compound of claim 1 and a pharmaceutically acceptable excipient.
13. A compound of the formula

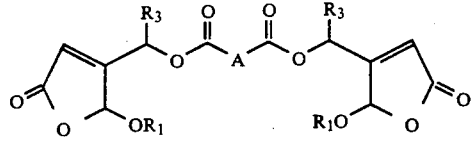

wherein
$R_1$ independently is H or alkyl of 1 to 20 carbons, $CO-R_2$, $CO-O-R_2$, $CO-NH-R_2$, where $R_2$ independently is H, alkyl of 1 to 20 carbons, phenyl, or lower alkyl substituted phenyl or halogen substituted phenyl;
A is $(CH_2)_n$ where n ranges between 0 to 30, or A is a a divalent branch chained alkyl radical, or cycloalkyl radical, having a total of 3 to 30 carbons;
$R_3$ independently is an alkyl group having 4 to 20 carbons, or a pharmaceutically acceptable salt thereof.

14. A compound of claim 13 wherein $R_1$ is H or $CH_3CO$.
15. A compound of claim 14 wherein A is $(CH_2)_n$ and n is an integer in the range of 0 to 16.
16. A compound of claim 15 wherein n is 1.
17. A compound of claim 16 wherein $R_3$ is $(CH_2)_{11}CH_3$.
18. The compound of claim 17 wherein $R_1$ is H.
19. A compound of claim 16 wherein $R_3$ is $(CH_2)_5CH_3$.
20. The compound of claim 19 wherein $R_1$ is H.
21. A compound of claim 15 wherein n is 3.
22. A compound of claim 21 wherein $R_3$ is $(CH_2)_{11}CH_3$.
23. The compound of claim 22 wherein $R_1$ is H.
24. A compound of the formula

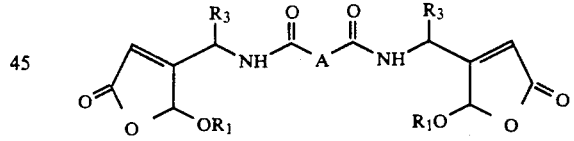

wherein
$R_1$ independently is H or alkyl of 1 to 20 carbons, $CO-R_2$, $CO-O-R_2$, $CO-NH-R_2$, where $R_2$ independently is H, alkyl of 1 to 20 carbons, phenyl, or lower alkyl substituted phenyl or halogen substituted phenyl;
A is $(CH_2)_n$ where n ranges between 0 to 30, or A is a a divalent branch chained alkyl radical, or cycloalkyl radical, having a total of 3 to 30 carbons;
$R_3$ independently is an alkyl group having 4 to 20 carbons, or a pharmaceutically acceptable salt thereof.

25. A compound of claim 24 wherein $R_1$ is H or $CH_3CO$.
26. A compound of claim 25 wherein A is $(CH_2)_n$ and n is an integer in the range of 0 to 16.
27. A compound of claim 26 wherein n is 3.
28. A compound of claim 27 wherein $R_3$ is $(CH_2)_{11}CH_3$.
29. The compound of claim 28 wherein $R_1$ is H.

* * * * *

UNITED STATES PATENT AND TRADEMARK OFFICE
CERTIFICATE OF CORRECTION

PATENT NO. : 5,169,963

DATED : December 8, 1992

INVENTOR(S) : Gary C. M. Lee

It is certified that error appears in the above-identified patent and that said Letters Patent is hereby corrected as shown below:

ON THE TITLE PAGE:

In the Abstract, first line after the structure, "1 - 29" should be —1 - 20—;

Column 2, line 42, "Which" should be —which—;

Column 3, line 5, before "processes" insert —the—;

Column 3, line 41, "With" should be —with—;

Column 4, line 25 (approximately), "Formula 6" (first occurrence in Scheme) should be —Formula 5—;

Column 5, line 22, after "-4-" insert —(— before the "1";

Column 9, line 65, "(1000 ug/ml)" should be —(100 ug/ml)—; and

Column 16, line 55, Claim 24, "$(Ch_2)_n$" should be —$(CH_2)_n$—.

UNITED STATES PATENT AND TRADEMARK OFFICE
CERTIFICATE OF CORRECTION

PATENT NO. : 5,169,963

DATED : December 8, 1992

INVENTOR(S) : Gary C. M. Lee

It is certified that error appears in the above-identified patent and that said Letters Patent is hereby corrected as shown below:

Column 2, line 48, delete "a" second occurrence;

Column 15, line 56, Claim 1, delete "a" second occurrence; and

Column 16, line 22, Claim 13, delete "a" second occurrence.

Signed and Sealed this

Fourth Day of January, 1994

*Attest:*

BRUCE LEHMAN

*Attesting Officer*  Commissioner of Patents and Trademarks